United States Patent [19]

Shin et al.

[11] Patent Number: 5,224,981

[45] Date of Patent: * Jul. 6, 1993

[54] METHODS AND COMPOSITIONS FOR TREATING PLANTS EXPOSED TO SALT

[75] Inventors: Charles C. Shin; Nicolai A. Favstritsky, both of Lafayette, Ind.

[73] Assignee: Great Lakes Chemical Corporation, W. Lafayette, Ind.

[*] Notice: The portion of the term of this patent subsequent to Mar. 2, 2009 has been disclaimed.

[21] Appl. No.: 852,815

[22] Filed: Mar. 17, 1992

[51] Int. Cl.$^5$ .............................................. A01N 43/08
[52] U.S. Cl. ............................. 504/294; 71/DIG. 1; 504/140
[58] Field of Search ............................................. 71/88

[56] References Cited

U.S. PATENT DOCUMENTS 4,615,725 10/1986 Weissmuller et al. .................. 71/88
4,886,543 12/1989 Shin et al. ............................... 71/88

Primary Examiner—Glennon H. Hollrah
Assistant Examiner—B. Bembenick
Attorney, Agent, or Firm—Woodard, Emhardt, Naughton, Moriarty & McNett

[57] ABSTRACT

Methods and compositions for the protection of plant tissue from damage upon exposure to chemical stresses, and to assist plant tissue in recovering from chemical stress injuries, include the application of an effective amount of chemical stress-protectant compositions selected from the group consisting of tetrahydrofurfuryl alcohol, tetrahydrofurfuryl amine and mixtures thereof. The compositions are applied as aqueous solutions containing between about 0.005 and about 25 wt % of the stress-protectant components. Surfactants may be included to improve application of the compositions to the plant tissues.

23 Claims, No Drawings

METHODS AND COMPOSITIONS FOR TREATING PLANTS EXPOSED TO SALT

BACKGROUND OF THE INVENTION

1. Field of the Invention

The present invention relates to methods and compositions for the treatment of plants to reduce injury due to exposure to certain chemical stresses, and more particularly to the application of compositions to plants to minimize or prevent stress injuries. The present invention further relates to the treatment of plants which have been subjected to injury due to exposure to the identified stresses.

2. Description of the Prior Art

Plants are subject to exposure to a variety of chemical stresses, which can result from high salt concentrations resulting from brackish water, or from pesticides, herbicides and the like. A great variety of chemicals, including those to which plants are not normally exposed, or those in unusually high concentrations, can have a severe impact on the growth and productivity of plants.

It has been known for a long time that an excessive amount of chemical in the root environment reduces the growth of plants and results in low crop yield. The response to chemical concentration differs greatly among various plant species. One of the worst common chemicals affecting the growth of plants and low crop yield is NaCl. Stress resulting from exposure to NaCl substantially decreases the crop yield. It has been reported that water uptake in wheat and barley was substantially decreased by increasing salinity stress. However, whether the effect is on water deficits or on high internal electrolyte concentration is not yet known.

Of the 14 billion hectares of available land in the world, only one-fourth of it is potentially arable. Nearly 25% of this arable land is subject to salinity. Due to rapid urban development, matters are getting worse. Salt water is creeping into fresh water, and water reservoirs are becoming contaminated with chemicals and excess salt.

Techniques have been exploited in vitro to isolate salt tolerant plants and to probe the physiological mechanism of salt tolerance. A plant hormone, abscisic acid, has been reported to accelerate the growth of rice cells exposed to ionic salt, but not to water deficits elicited by non-ionic chemicals. None of the known prior art methods has been shown to be practical in alleviating stress of plants from excess ionic or nonionic salts. The purpose of this invention is to develop a chemical agent and method to alleviate injuries of plants exposed through foliage contact and root environment to stressful concentrations of chemicals.

It is desirable to treat plants to avoid any detrimental affects that would otherwise result under these circumstances. In order to be practically useful, a chemical composition used to treat plants against these stress injuries must be non-toxic to the plants, environmentally acceptable and relatively inexpensive. The present invention satisfies these requirements and provides for the protection of plants from chemical stresses of the types previously mentioned.

SUMMARY OF THE INVENTION

In accordance with this invention, there are provided methods and compositions for protecting plants and plant products from certain chemical stresses, and for promoting recovery of plants from stress injuries. A plant anti-stress chemical composition has been discovered which comprises an aqueous solution containing an effective amount of a chemical component selected from the group of tetrahydrofurfuryl alcohol, tetrahydrofurfuryl amine, and mixtures thereof. The solution is applied to the plant surfaces and tissues prior to and/or after exposure to the stress. The solution preferably includes between about 0.005 and about 25 wt. % of the stress protectant.

Among the objects of this invention is the provision of compositions and methods to protect plants and plant products from damage due to certain chemical stresses, e.g., those which occur upon exposure to excessive levels of salt and other chemicals.

Another object is the provision of an effective method for treating plants and plant products injured due to exposure to such chemical stresses.

A further object of this invention is to provide such stress protectant compositions and methods which are relatively inexpensive, non-toxic and environmentally acceptable.

These and other objects and features of this invention will be apparent from the description hereafter.

DESCRIPTION OF THE PREFERRED EMBODIMENTS

For the purposes of promoting an understanding of the principles of the invention, reference will now be made to the preferred embodiment of the invention and specific language will be used to describe the same. It will nevertheless be understood that modifications and further applications of the principles of the invention are contemplated as would normally occur to one skilled in the art to which the invention relates.

Exposure of plant tissue to a variety of chemical stresses can result in serious damage. Such forms of chemical stress which can adversely affect plant tissue include stresses due to exposure to herbicides, pesticides and the like, high salt concentrations such as resulting from brackish water, and any other stress resulting from chemicals which are of a type or are at a concentration to which plants are intolerant. As used herein, the term "chemical stress" includes each of the foregoing forms of plant stress. The term "plant tissue" is used to indicate either plants or plant products subject to damage by exposure to the identified chemical stress. The present invention is not directed to the treatment of plants which have been exposed to chilling or freezing temperatures.

The extent and nature of damage resulting from exposure to the chemical stresses is exemplified by the effect of salinity on plants. Salt stress can reduce plant growth, resulting in lower weight gain of the plant, as well as reduced crop production. The impact of plant tissue treatments in regard to salt stress is an appropriate and useful model for demonstrating the efficacy of compositions and methods on the protection of plant tissue from chemical stresses addressed by the present invention.

In accordance with this invention, a plant tissue, stress-protectant composition has been discovered which comprises an aqueous solution containing a stress-protectant component selected from the group consisting of tetrahydrofurfuryl alcohol, tetrahydrofurfuryl amine, and mixtures thereof. Preferably, the composition comprises an aqueous solution comprising between about 0.005 and about 25 wt. percent of the stress-protectant component, and most preferably comprises between about 0.05 and about 5 wt. percent of the stress-protectant component. It has also been discovered that the stress-protectant composition is effective in promoting a recovery of plant tissue from the chemical stresses.

Tetrahydrofurfuryl alcohol is a colorless, high boiling, primary alcohol having the following structure:

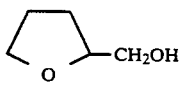

Tetrahydrofurfuryl amine is a colorless, high boiling, primary amine having the following structure:

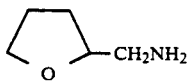

Both tetrahydrofurfuryl alcohol and tetrahydrofurfuryl amine exhibit stress-protectant properties as against exposure to the described chemical stresses. However, tetrahydrofurfuryl alcohol is preferred in accordance with the present invention.

Tetrahydrofurfuryl alcohol (THFA) is produced by the hydrogenation of furfuryl alcohol. As expected on the basis of its structure, tetrahydrofurfuryl alcohol exhibits behavioral characteristics of both alcohol and ethers. Due to its cyclic ether structure, tetrahydrofurfuryl alcohol possesses distinctly unique solvent properties which are desirable. THFA is low in volatility (vapor pressure is 2.3 mm Hg at 39° C.), non-damaging and non-toxic, biodegradable, easily absorbable, able to penetrate membranes, considerably soluble in water, in addition to forming multiple hydrogen bonds, and able to dissolve electrolytes. Tetrahydrofurfuryl amine has similarly useful characteristics.

The resistance of plant tissues to chemical stresses is increased through the application of the stress-protectant compositions of this invention, such as by spraying or root drenching methods. The composition is applied at moderate, ambient temperatures, i.e., at temperatures of the air surrounding the plant tissues above a chilling temperature. Any conventional apparatus suitable for aqueous solutions may be employed for the foregoing application methods. For spraying, the plant tissues to be treated are thoroughly sprayed so that all of the plant tissue surfaces are substantially covered. Due to the size, shape and/or other characteristics (such as surface properties) of a plant, an application may require two or more sprayings.

The compositions may be formulated and supplied to the user ready to apply, or in concentrated form and diluted to the desired strength prior to application to the plant tissues. No special handling or mixing steps are required. THFA and tetrahydrofurfuryl amine are stable in aqueous solution. Moreover, these compositions are stable to light and do not need to be stored in an opaque container nor prepared immediately prior to application.

Since aqueous THFA or tetrahydrofurfuryl amine solutions, or mixtures thereof, may not completely wet the surfaces of some plant tissues, such as leaves having waxy surfaces, it is preferred for some applications that the compositions include non-ionic surfactants. Suitable surfactants operate as penetrating agents and otherwise may be inert, or at least non-interfering, components.

For example, two different surfactants, polyoxyethylene sorbitan monolaurate (Tween 20) and polyoxyethylene sorbitan monooleate (Tween 80) have been found to improve the effectiveness of the compositions in appropriate circumstances. When non-ionic surfactants are used, it is preferred that the stress-protectant composition contain between about 0.005 and about 0.5 wt. percent of the non-ionic surfactant.

The stress-protectant compositions of the present invention may be applied to the plant tissues from immediately prior to 24 hours prior to exposure to the stress conditions, and preferably at least about 4 or more preferably at least about 12 hours prior to exposure. For optimal results it is preferred that the stress-protectant compositions be repeatedly applied prior to exposure to the stress. For additional protection, the stress-protectant compositions may be applied immediately after the stress exposure to help the plant tissues recover from any stress injuries that are incurred. For maximum protection during extended periods of exposure to stress conditions, it may be desirable to apply the stress-protectant compositions periodically, such as weekly.

The following examples serve to further illustrate the invention, with all percentages being by weight unless otherwise indicated. It will be appreciated that these examples are demonstrative only, and the applicability of the compositions and methods described therein extends to the various other plants, as well as the differing types of chemical stresses, elsewhere described herein.

EXAMPLE 1

The efficacy of the present invention is readily demonstrated by the results of experiments showing reduction in plant injuries induced by salt stress. The salt solution chosen for this study was an aqueous solution of NaCl and $MgCl_2$, which are two major components of sea water. The concentrations of NaCl and $MgCl_2$ in average sea water are 0.43 mole/Kg for NaCl and 0.054 mole/Kg for $MgCl_2$. Total ionic salt concentration in sea water is 3.5%. An aqueous solution was prepared using reagent grade NaCl and $MgCl_2$ in the approximate concentrations of average sea water, and with a total salt concentration of 3.75%.

Fifty-four uniform pepper plants (c.v. Ma Belle) in 9 oz. plastic cups were selected for the experiment. One-half of the plants (27 plants) was treated with an aqueous mixture solution of 0.25% THFA and 0.1% Tween 20, and the remaining 27 plants were treated with an aqueous solution 0.1% Tween 20. The treatment was made by foliage spraying until it started to drip.

Twenty-four hours after the treatment, the plants underwent salt stress. All 54 plants were given 15 ml of the 3.75% aqueous solution of NaCl and $MgCl_2$. The treatment and stress procedure was repeated every seven days for four weeks, after which normal greenhouse care and watering were resumed. Survival rate was determined after 14 days. Fourteen plants out of the 27 plants treated with the aqueous solution of 0.25% THFA and 0.1% Tween 20 survived, whereas only three plants out of the 27 non-treated plants survived.

All surviving plants were transplanted from the 9 oz. plastic cups to 8" plastic pots. The plants were moved from an indoor greenhouse to an outdoor vinyl top greenhouse for harvest. After the transplanting, all three of the non-treated plants and six of the treated plants died, leaving eight treated plants for observation.

EXAMPLE 2

The foregoing procedures are repeated for other stress-protectant compositions of the present invention. For example, the anti-stress agents include:

1. tetrahydrofurfuryl alcohol dissolved in deionized (DI) water to make 0.05% and 0.5% THFA aqueous solutions;
2. 0.1 parts of a surfactant, polyoxyethylene sorbitan monolaurate (Tween 20), and 0.05–0.5 parts tetrahydrofurfuryl alcohol dissolved in 99.40–99.85 parts DI water to make an aqueous 0.05–0.5% THFA +0.1% Tween 20 solution;
3. tetrahydrofurfuryl amine dissolved in DI water to make 0.3% tetrahydrofurfuryl amine aqueous solution;
4. 0.10 parts of a surfactant, Tween 20, and 0.3 parts of tetrahydrofurfuryl amine dissolved in 99.60 parts of DI water to make an aqueous 0.3% tetrahydrofurfuryl amine+0.10% Tween 20 solution; and
5. the foregoing solutions 2 and 4, except using Tween 80.

Application of the foregoing compositions to the plant tissues, prior to exposure to the salt stresses, provides protection against stress injuries. The treated plants display better growth than the untreated plants.

Protection of the plants is also obtained upon treatment with aqueous solutions containing as low as 0.005 wt. % and as high as 25 wt. % of the tetrahydrofurfuryl amine, as well as mixtures of the alcohol and the amine yielding total weight percentages as indicated. Generally, treatments with the amine and mixtures of the amine and the alcohol give comparable results to treatments with the tetrahydrofurfuryl alcohol solutions alone. Treatment with Tween 20 or Tween 80 alone has no effect on protecting plants from chemical stress injuries.

EXAMPLE 3

The foregoing procedures are repeated for other chemical stresses, including stress due to exposure to excessive concentrations of herbicides, pesticides and other ionic and non-ionic chemicals. Protection of the plants is also obtained upon treatment with the various protectant compositions of Examples 1 and 2.

EXAMPLE 4

Treatment with the inventive compositions of plants which have already received chemical stress injuries also contributes to plant recovery and improved plant growth. Plants, injured from the various chemical stresses as set forth in Example 3, which are treated immediately following exposure to the injurious stresses, display better growth and development than untreated plants.

While the invention has been described in detail in the foregoing description and its specific Examples, the same is to be considered as illustrative and not restrictive in character. Only the preferred embodiments have been described, and all changes and modifications that come within the spirit of the invention are desired to be protected.

What is claimed is:

1. A method for increasing the resistance of plant tissue to damage upon exposure to NaCl and MgCl thereby reducing damage to plant tissue upon exposure to NaCl and MgCl which comprises applying to the plant tissue an effective amount of a NaCl and MgCl stress-protectant composition selected from the group consisting of tetrahydrofurfuryl alcohol, tetrahydrofurfuryl amine and mixtures thereof.

2. The method of claim 1 in which said applying comprises applying an aqueous solution of the chemical stress-protectant composition.

3. The method of claim 2 in which the aqueous solution contains between 0.005 and 25 wt % of the chemical stress-protectant composition.

4. The method of claim 3 in which the aqueous solution contains between 0.05 and 5.0 wt % of the chemical stress-protectant composition.

5. The method of claim 2 in which the chemical stress-protectant composition consists essentially of an aqueous solution of tetrahydrofurfuryl alcohol.

6. The method of claim 5 in which the aqueous solution contains between 0.05 and 5.0 wt % of the tetrahydrofurfuryl alcohol.

7. The method of claim 2 in which the aqueous solution further contains a non-ionic surfactant.

8. The method of claim 7 in which the aqueous solution contains between 0.05 and 0.5 wt % of the non-ionic surfactant.

9. The method of claim 7 in which the non-ionic surfactant is selected from the group consisting of polyoxyethylene sorbitan monolaurate and polyoxyethylene sorbitan monooleate.

10. The method of claim 1 in which said chemical stress-protectant composition is applied a sufficient time prior to exposure to the stress to permit at least partial absorption of the composition by the plant tissue.

11. The method of claim 10 in which the chemical stress-protectant composition is applied at least about 4 hours prior to exposure of the plant tissue to the stress.

12. The method of claim 10 in which the chemical stress-protectant composition is applied at least about 12 hours prior to exposure of the plant tissue to the stress.

13. The method of claim 10 in which the chemical stress-protectant composition is applied to the plant tissue at least twice prior to exposure of the plant tissue to the stress.

14. The method of claim 10 in which the chemical stress-protectant composition is also applied to the plant tissue after exposure of the plant tissue to the stress.

15. A method for the treatment of plant tissue injured due to exposure to NaCl and MgCl which comprises applying to the plant tissue an effective amount of a NaCl and MgCl stress-recovery composition selected from the group consisting of tetrahydrofurfuryl alcohol, tetrahydrofurfuryl amine and mixtures thereof.

16. The method of claim 15 in which said applying comprises applying an aqueous solution of the stress-recovery composition.

17. The method of claim 16 in which the aqueous solution contains between 0.005 and 25 wt % of the stress-recovery composition.

18. The method of claim 17 in which the aqueous solution contains between 0.05 and 5.0 wt % of the stress-recovery composition.

19. The method of claim 18 in which the stress-recovery composition consists essentially of an aqueous solution of tetrahydrofurfuryl alcohol.

20. The method of claim 19 in which the aqueous solution contains between 0.05 and 5.0 wt % of the tetrahydrofurfuryl alcohol.

21. The method of claim 16 in which the aqueous solution further contains a non-ionic surfactant.

22. The method of claim 21 in which the aqueous solution contains between 0.05 and 0.5 wt % of the non-ionic surfactant.

23. The method of claim 21 in which the non-ionic surfactant is selected from the group consisting of polyoxyethylene sorbitan monolaurate and polyoxyethylene sorbitan monooleate.

* * * * *